(12) United States Patent
Harman et al.

(10) Patent No.: US 9,090,884 B2
(45) Date of Patent: Jul. 28, 2015

(54) FORMULATIONS OF VIABLE MICROORGANISMS AND THEIR METHODS OF PRODUCTION AND USE

(75) Inventors: Gary E. Harman, Geneva, NY (US); Daniel B. Custis, Van Wert, OH (US)

(73) Assignees: Advanced Biological Marketing Incorporated, Van Wert, OH (US); Cornell Research Foundation, Inc., Ithaca, NY (US)

( * ) Notice: Subject to any disclaimer, the term of this patent is extended or adjusted under 35 U.S.C. 154(b) by 1726 days.

(21) Appl. No.: 11/517,051

(22) Filed: Sep. 7, 2006

(65) Prior Publication Data

US 2011/0027232 A1 Feb. 3, 2011

Related U.S. Application Data

(60) Provisional application No. 60/715,076, filed on Sep. 8, 2005.

(51) Int. Cl.
| | | |
|---|---|---|
| *A01N 63/00* | (2006.01) |
| *A01N 63/04* | (2006.01) |
| *C12N 1/20* | (2006.01) |
| *C12N 1/14* | (2006.01) |
| *C12N 1/04* | (2006.01) |

(52) U.S. Cl.
CPC ........ *C12N 1/20* (2013.01); *A01N 63/00* (2013.01); *A01N 63/04* (2013.01); *C12N 1/04* (2013.01); *C12N 1/14* (2013.01)

(58) Field of Classification Search
None
See application file for complete search history.

(56) References Cited

U.S. PATENT DOCUMENTS

| | | | |
|---|---|---|---|
| 4,670,248 A * | 6/1987 | Schricker | 424/438 |
| 4,711,656 A * | 12/1987 | Kaneshiro | 71/7 |
| 5,041,383 A | 8/1991 | Paau et al. | |
| 5,188,634 A | 2/1993 | Hussein | |
| 5,215,747 A * | 6/1993 | Hairston et al. | 424/93.462 |
| 5,300,127 A * | 4/1994 | Williams | 47/57.6 |
| 5,503,651 A | 4/1996 | Kloepper et al. | |
| 5,503,652 A | 4/1996 | Kloepper et al. | |
| 5,696,541 A | 12/1997 | Kosanke et al. | |
| 5,697,186 A | 12/1997 | Neyra et al. | |
| 5,798,252 A | 8/1998 | Hobsen et al. | |
| 5,888,947 A | 3/1999 | Lambert et al. | |
| 6,209,259 B1 | 4/2001 | Madigan et al. | |
| 6,606,822 B2 | 8/2003 | Bonfiglio | |
| 6,841,515 B2 | 1/2005 | Wertz et al. | |
| 6,900,162 B2 | 10/2005 | Babler et al. | |
| 7,157,254 B1 | 1/2007 | Akimoto et al. | |
| 7,213,367 B2 | 5/2007 | Wertz et al. | |
| 2003/0068303 A1 | 4/2003 | Selvig et al. | |
| 2004/0175389 A1 | 9/2004 | Porubcan | |
| 2004/0220056 A1 | 11/2004 | Glenn et al. | |
| 2005/0079342 A1 | 4/2005 | Ye | |
| 2006/0029576 A1 | 2/2006 | Huang et al. | |
| 2006/0240983 A1 | 10/2006 | Yamaguchi | |
| 2007/0243235 A1 | 10/2007 | David | |
| 2009/0093365 A1 | 4/2009 | Walsh et al. | |

FOREIGN PATENT DOCUMENTS

| | | |
|---|---|---|
| CN | 1276973 A * | 12/2000 |
| EP | 0286351 | 10/1988 |
| EP | 0594125 | 4/1994 |
| EP | 603989 A2 * | 6/1994 |
| WO | WO9419924 | 9/1994 |
| WO | WO9604221 | 2/1996 |
| WO | WO03000051 A2 | 1/2003 |
| WO | WO03020837 | 3/2003 |
| WO | WO2004005219 | 1/2004 |
| WO | WO2005030383 | 4/2005 |

OTHER PUBLICATIONS

Cole-Parmer "Cole-Parmer's FoodTechSource: Water Activity", Cole-Parmer Instrument Company, 2002, retreived from internet <http://www.foodtechsource.com/rcenter/tech_data/td_water.htm>, 3 pages (HTML text).*
Garrity,G.M., Kuykendall, L.D., et al "Class I,Order VI, Family VII. Bradyrhizobiaceae fam. nov.: Genus I. *Bradyrhizobium*" Bergey's Manual of Systemativc Bacteriology, 2nd ed. 2005, vol. 2, chapter 32, pp. 438-443.*
Jin, Xixuan and Custis, Daniel "Microencapsulating Aerial Conidia of Trichoderma harzianum Through Spray Drying at Elevated Temperatures" Biological Control, 56(2), Feb. 2011 (online Nov. 14, 2010), pp. 202-208, doi:10.1016/j.biocontrol.2010.11.008.*
Schisler et al., "Formulation of *Bacillus* spp. for Biological Control of Plant Diseases," Phytopathology 94:1267-1271 (2004).
Zohar-Perez C. et al, "Mutual relationship between soils and biological carrier systems", Biotechnology and Bioengerineering, vol. 92, No. 1, Oct. 2005, pp. 54-60., XP002550257, ISSN: 0006-3592.
Pedreschi F. et al., "Viablity of dry Trichoderma harzianum spores under storage", Bioprocess Engineering, vol. 17, No. 3 1997, pp. 177-183, XP002550258, ISSN 0178-515X.

* cited by examiner

*Primary Examiner* — Rosanne Kosson
*Assistant Examiner* — Aaron J Kosar
(74) *Attorney, Agent, or Firm* — Standley Law Group LLP

(57) ABSTRACT

The present invention relates to formulations of viable microorganisms in a water insoluble, water-absorbent substance and methods of producing formulations of viable microorganisms. Also disclosed is a method of treating plants and/or plant seeds with the formulations of the present application.

13 Claims, 2 Drawing Sheets

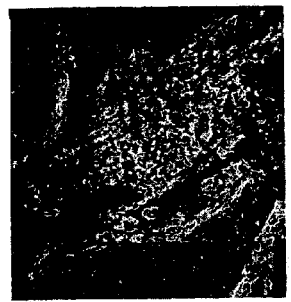
Figure 1
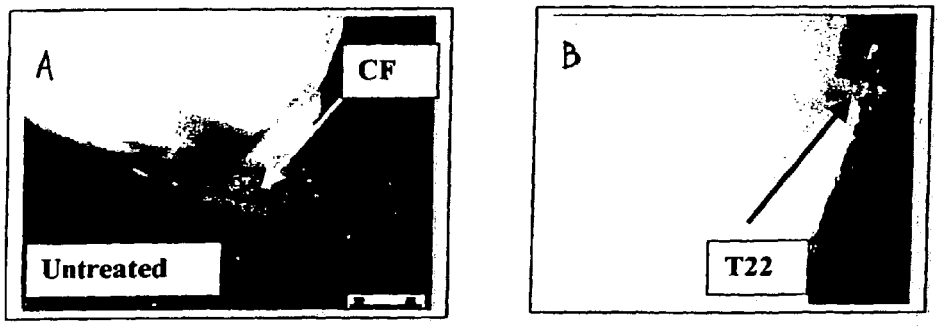
Figures 2A-B

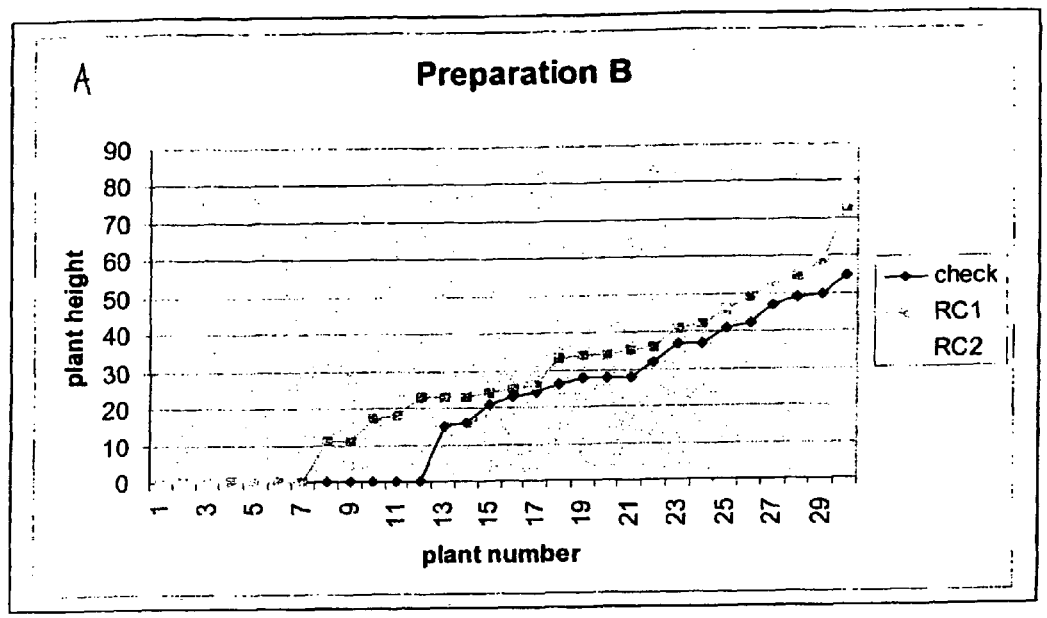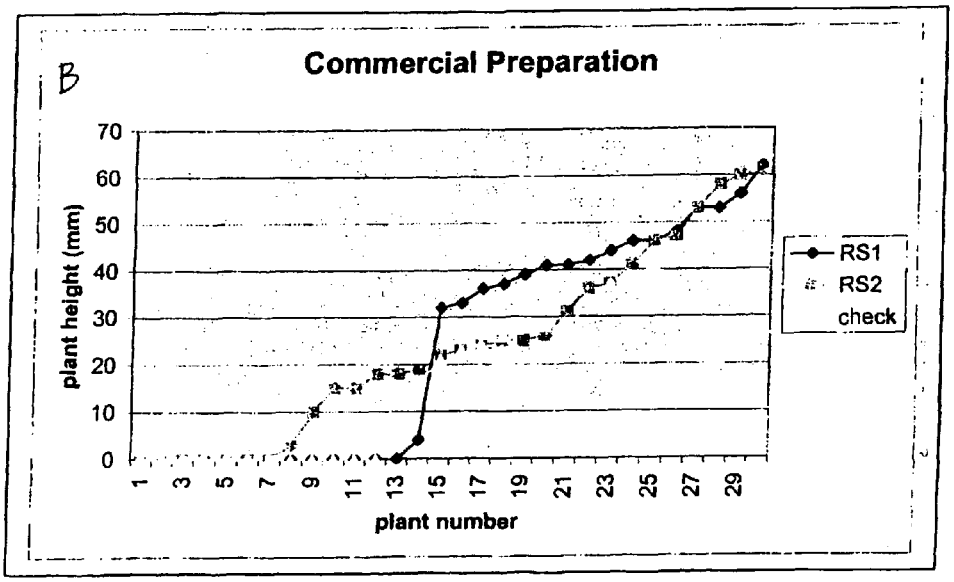
Figures 3A-B

FORMULATIONS OF VIABLE MICROORGANISMS AND THEIR METHODS OF PRODUCTION AND USE

This application claims the priority benefit of U.S. Provisional Patent Application Ser. No. 60/715,076, filed Sep. 8, 2005, which is hereby incorporated by reference in its entirety.

FIELD OF THE INVENTION

The present invention relates to formulations of viable microorganisms and their methods of production and use.

BACKGROUND OF THE INVENTION

Certain microorganisms are produced in large quantities and can be formulated for various commercial uses. For example, microbial products have been used in agriculture to protect plants from pests and diseases, to improve plant performance and nutrition, and as inoculants for silages. These microbial products must be produced in a way that is efficient, free of contamination, and suitable for maintaining high levels of viable microorganisms. Production of microbial formulations for commercial use requires drying the microorganisms in a way that preserves viability of the microbes, provides a suitable medium for commercial use, and maintains an extended shelf life of the microbial product.

A range of microorganisms have been produced and formulated for commercial use. Examples of commercially formulated microorganisms include strains of *Lactobacillus* spp. for a variety of food, probiotic, and animal feed uses; entornophagous fungi, such as *Beaveria* and *Metarhizum* spp., for control of plant-attacking insects; fungi that protect plants from diseases, such as *Trichoderma* and *Clonostachys* spp.; bacteria that protect plants from disease, such as *Pseudomonas* and *Bacillus* spp., as well as *Rhizobium* and *Bradyrhizobium*; and related bacteria that fix nitrogen through a symbiotic relationship with legumes and fungi, such as *Colletotrichum* spp., which are used as weed controls by causing disease in weeds. These uses of microorganisms are well documented (Hornby et al., *Biological Control of Soil-Borne Plant Pathogens*, Wallinford, U.K. (1990); TeBeest, *Microbial Control of Weeds*, New York, Chapman and Hall (1991); Vurro et al., *Enhancing Biocontrol Agents and Handling Risks*, IOS Press, Amsterdam (2001)).

Microorganisms formulated for commercial use are usually produced in liquid (submerged) fermentation systems (Jin et al., *Principles in the Development of Biological Control Systems Employing Trichoderma Species Against Soilborne Plant Pathogenic Fungi*, p. 174-195 In Leatham, G. F. (ed) *Symposium on Industrial Mycology*, Mycological Soc. Am., Brock/Springer Series in Contemporary Bioscience (1992); Stowell, "Submerged Fermentation of Biological Herbicides, Microbial Control of Weeds," D. O. TeBeest. New York, Chapman and Hall (1991); Jin et al., "Conidial Biomass and Desiccation Tolerance in *Trichoderma harzianum*," *Biological Control* 1:237-243 (1992); Jin et al., "Development of Media and Automated Liquid Fermentation Methods to Produce Desiccation-tolerant Propagules of *Trichoderma harzianum*," *Biol. Cont.* 7:267-274 (1996); Agosin et al., "Industrial Production of Active Propagules of *Trichoderma* for Agricultural Uses," *Trichoderma and Gliocladium*, Vol. 2. G. E. Harman and C. P. Kubicek. London, Taylor & Francis pp. 205-227 (1998)) or in semi-solid fermentation.

In all cases, the microorganisms are dried to a level that prevents rapid deterioration of the propagules and/or growth of contaminating microbes (Jin et al., "Conidial Biomass and Desiccation Tolerance in *Trichoderma harzianum*," *Biological Control* 1:237-243 (1992)). Typical drying methods include convective drying (e.g., spray drying or fluidized beds) and static heating. All of these drying methods have the potential to damage sensitive cells or spores of microorganisms. The physiology of spores produced by microorganisms may dramatically influence the methods that can be used to dry the biomass (Agosin et al., "Industrial Production of Active Propagules of *Trichoderma* for Agricultural Uses," *Trichoderma and Gliocladium*, Vol. 2. Harman and Kubicek, London, Taylor & Francis pp. 205-227 (1998)). Similarly, microorganisms differ substantially in the types of resistant propagules that are produced. For example, endospores of *Bacillus* spp. are hardy enough to withstand relatively high temperatures and rough physical handling without loss of viability. Commercial formulations of these bacteria typically have long shelf-lives. In contrast, some microorganisms produce no resistant spores and exist only as vegetative cells. These microorganisms, which have a shorter shelf-life, include *Pseudomonas* and *Bradyrhizobium* spp. Microorganisms which are intermediate in sensitivity include fungal spores, such as conidia, or species of *Trichoderma*, *Clonostaehys*, and *Colletotrichum*.

One strain of *Trichoderma*, *T. harzianum* strain T22, enjoys relatively wide use in commercial agriculture (Harman, "The Myths and Dogmas of Biocontrol. Changes in Perceptions Derived from Research on *Trichoderma harzianum* T-22," *Plant Disease* 84:373-393 (2000)). This microbe has been produced in large quantities and formulated on a clay-based medium. Formulations of this microbe have the disadvantage of being difficult to suspend in water for spray applications, slurry seed treatment formulations, or drench applications in greenhouses. Formulations of this microbe are also limited in their ability to form mixtures with chemical pesticides and biological products. An attempt was made to produce a dry formulation of *T. harzianum* strain T22 in combination with the chemical fungicide mancozeb. The combination of mancozeb and T22, when applied to potato seed pieces, resulted in improved yield and quality (size) of the potatoes in the succeeding crop. However, the dynamics of potato seed treatment require that any products being applied need to be formulated into a single dry preparation. When T22 and mancozeb were mixed together and stored in a dry formulation, the shelf life of T22 was reduced from about 6 months in the absence of the fungicide to only about 1 month in its presence. This problem has thus far been a major factor as to why T22 is not used significantly as a potato seed treatment.

New and improved methods of producing formulations of viable microorganisms having high activity levels and an extended shelf life are needed. Formulations of microorganisms, to be commercially useful, need to be capable of being suspended in water and mixed with other biological agents or chemical pesticides without toxic implications on the microorganism. Furthermore, it would be useful to formulate biological agents with a food base to help the microbes grow rapidly and to be highly competitive when applied. Current formulations permit growth of competitive microbes on any added food base. Processing methods that avoid damage to delicate microbial cells or spores are also needed.

The present invention is directed to overcoming these and other limitations in the art.

SUMMARY OF THE INVENTION

One aspect of the present invention relates to a method of producing a formulation of viable microorganisms. This method involves providing an aqueous suspension of viable microorganisms and combining the aqueous suspension with a water insoluble, water-absorbent substance under conditions effective to produce a formulation of viable microorganisms.

Another aspect of the present invention relates to a formulation of viable microorganisms. The formulation includes a water insoluble, water-absorbent substance, where the water insoluble, water-absorbent substance is present in an amount of at least about 90% by total weight of the formulation. The formulation also includes microorganisms mixed with the water insoluble, water-absorbent substance, with the microorganisms being present in the formulation in an amount of at least about $5 \times 10^8$ colony forming units per gram of formulation.

A further aspect of the present invention relates to a preparation of viable microorganisms including the formulation as described supra, suspended in a solution.

Yet another aspect of the present invention relates to method of treating a plant or a plant seed with a microorganism. This method involves providing a preparation or a formulation as described supra and applying the preparation or the formulation to a plant or plant seed under conditions effective to treat the plant or plant seed.

The present invention describes a simple process of drying and formulating fungal and bacterial microorganisms that is inexpensive, requires little equipment, and provides products with excellent viability and which are amenable to commercial use. The formulations of the present invention possess sufficient activity of the microorganism to be effective in a variety of applications, including applications that require suspension in water, such as spray, drip irrigation, and other water-based deliver system applications. The formulations of the present invention are nondusty and have a high level of cosmetic appeal. The shelf life of the formulations of the present invention is significantly longer than the shelf life of current formulations. Formulations of the present invention are also protected from the toxic effects of other biological agents or chemicals (e.g., pesticides), providing the opportunity to produce co-formulations of these materials. In addition, the formulations of the present invention contain a barrier to prevent growth of undesirable microorganisms which increases the biological efficacy of the desired microorganism. The method of the present invention reduces the amount of downstream processing and, therefore, minimizes the amount of damage that delicate microbial cells or spores may sustain.

The method of the present invention achieves significant advantages by providing gentle, but relatively rapid drying of microorganisms, which avoids elevated temperatures. The process is inexpensive. Further, the present invention makes it possible to simultaneously dry and encapsulate microbial cells.

BRIEF DESCRIPTION OF THE DRAWINGS

FIG. 1 is a photomicrograph showing precipitating cellulose fibers covered with *Trichoderma conidia*.

FIGS. 2A-B are photomicrographs showing the growth of T22 on maize seeds (3 days of germination) on blotters. Contaminating fungi were observed on every nontreated seed (FIG. 2A) but only rarely on seeds treated with T22 (FIG. 2B).

FIGS. 3A-B are graphs comparing different preparations of T22 as applied to maize inbred line Mo17. The cfu levels of preparation B (FIG. 3A) was $2.4 \times 10^9$, while the cfu level of the commercial preparation (FIG. 3B) was one order of magnitude lower.

DETAILED DESCRIPTION OF THE INVENTION

One aspect of the present invention relates to a method of producing a formulation of viable microorganisms. This method involves providing an aqueous suspension of viable microorganisms and combining the aqueous suspension with a water insoluble, water-absorbent substance under conditions effective to produce a formulation of viable microorganisms.

Many beneficial microorganisms can be dried and formulated pursuant to the methods of the present invention. Microorganisms may include, without limitation, species from the kingdoms Eubacteria, Archaebacteria, Protista, and Fungi. In addition to the microorganisms themselves, propagules of the microorganisms may also be formulated pursuant to the methods of the present invention. Propagules include, without limitation, fungal spores, hyphae, vesicles, and auxiliary cells. The microorganisms may have a commercial utility in agricultural applications and are useful to control insect pests, weeds, and plant disease, or to provide nourishment to plants so that their growth and/or yield is increased. Suitable species of microorganisms include, without limitation, species of the genera *Bacillus* and *Pseudomonas* (useful for insect control); *Beauveria, Metarhizum*, and species of the division Oomycota (weed control); *Colletotrichum, Phytophthora, Trichoderma, Clonostachys*, and binucleate *Rhizoctonia* (to control plant diseases); and *Bradyrhizobium, Rhizobium* and related genera (to improve plant nutrition and yield including). Other similar microorganisms can also be formulated using the method of the invention. Microorganisms with commercial utility in food processing, brewing, and silage and sewage treatment are also suitable for formulation pursuant to the method of the present invention.

Preferred microorganisms include species of the fungus *Trichoderma* and species of the bacteria *Bradyrhizobium*.

According to the method of the present invention, viable microorganisms are provided in an aqueous suspension, or an otherwise suitable environment for maintaining the viability of the microorganisms to be formulated. Aqueous suspensions of microorganisms are commonly known and can be prepared according to methods known by those of ordinary skill in the art. Large-scale production and/or fermentation of microorganisms is widely known.

Viable microorganisms, typically suspended in a solution, are combined with a water insoluble, water-absorbent substance according to the method of the present invention. The water insoluble, water-absorbent substance can be any organic or inorganic material capable of removing moisture gently from the suspension of viable microorganisms. Suitable inorganic substances include zeolite, porous beads or powders, silica, and the like. Suitable organic substances include plant materials, such as ground agricultural products (e.g., corn cobs), porous wood products, cellulose, and the like. In addition, cyclodextrins may be useful as water insoluble, water-absorbent substances. Cyclodextrins are widely used in many industries for encapsulation/binding of a wide variety of relatively apolar materials. Cyclodextrins are inexpensive, available in bulk quantities, and have low solubility in water (depending upon the actual composition of the cyclodextrin molecule). Cyclodextrins can be used as formulating agents to sequester liquid or apolar solid materials that can be suspended in water, such as pesticides and pesticide adjuvants. Any combination of the above-described water insoluble, water-absorbent substances may also be used. In a preferred embodiment, the water insoluble, water-absorbent substance is a finely ground cellulose powder.

The water insoluble, water-absorbent substance is combined with the aqueous suspension of viable microorganisms to an amount of about 80 to 99% by total weight of the formulation. Thus, the aqueous suspension of viable microorganism is present in the formulation in an amount of about 1 to 20% by total weight of the formulation. Preferably, the water insoluble, water-absorbent substance is present in the formulation in the amount of at least about 80%, 85%, 90%, 95%, or 99% by total weight of the formulation.

Combining the aqueous suspension of viable microorganisms with the water insoluble, water-absorbent substance can be carried out by a variety of methods. In a preferred embodiment, the combining step is carried out by kneading the aqueous suspension with the water insoluble, water absorbent substance in a flexible container or bag.

Combining the aqueous suspension of viable microorganisms with the water insoluble, water-absorbent substance is carried out to achieve a formulation of viable microorganisms having a water activity (Aw) at or below about 1.0.

According to one embodiment of the method of the present invention, the aqueous suspension of viable microorganisms can be contacted with an encapsulating material prior to combining the microorganisms with the water insoluble, water-absorbent substance. The encapsulating material will then encapsulate the microorganisms. In a preferred embodiment, the encapsulating material is a water soluble material capable of forming a film or microbead when dried. Suitable encapsulating materials include, without limitation, native or modified chitosans, native of modified starches, glucans or dextrins, celluloses modified so they are soluble, and any of a number of native or modified vegetable or microbial gums, including agars, guar, locust, carrageenan, xanthans, pectins, and the like, and combinations thereof. In a preferred embodiment, the encapsulating material is a dextrin, such as Crystal-Tex (National Starch and Chemical Co., Bridgewater, N.J.).

Encapsulating the microorganisms pursuant to the method of the present invention provides many advantages. In particular, encapsulated microorganisms are more resistant to chemical pesticides, which may dramatically reduce the shelf life of unencapsulated microorganisms by contact toxicity. For example, it may be desirable to combine formulations of microorganisms with other chemical or biological agents. When the microorganisms are placed together in a container with e.g., a chemical fungicide, the chemical fungicide would be detrimental to an unencapsulated microorganism. Thus, encapsulation prevents contact of the microorganisms with the chemical pesticide, unless the chemical pesticide has a significant vapor pressure. Encapsulation of the microorganisms may, therefore, be advantageous when formulating mixtures of microorganisms with chemical pesticides and other biological products.

Formulations of viable microorganisms produced by the method of the present invention can be dried. However, drying of the microorganisms requires methods that maintain the viability of the microorganisms. In a preferred embodiment, the drying method is air drying. Air drying is a method that prevents the microorganisms from coming into contact with high temperatures.

The method of the present invention can be carried out to produce formulations of viable microorganisms having at least about $5\times10^8$ to $1\times10^{12}$ colony forming units ("cfu") of microorganisms per gram of formulation. When the microorganism is fungi, formulations of viable microorganisms preferably have at least about $5\times10^8$ to $1\times10^{11}$ cfu. When the microorganism is bacteria, formulations of viable microorganisms preferably have at least about $5\times10^8$ to $1\times10^{12}$ cfu. When the microorganism is *Bacillus*, formulations of viable microorganisms preferably have at least about $5\times10^8$ to $1\times10^{12}$ cfu. In a preferred embodiment, the formulation has at least about $5\times10^8$ cfu per gram of formulation.

Another aspect of the present invention relates to a formulation of viable microorganisms. The formulation includes a water insoluble, water-absorbent substance, where the water insoluble, water-absorbent substance is present in an amount of at least about 90% by total weight of the formulation. The formulation also includes microorganisms mixed with the water insoluble, water-absorbent substance, with the microorganisms being present in the formulation in an amount of at least about $5\times10^8$ colony forming units per gram of formulation.

A further aspect of the present invention relates to a preparation of viable microorganisms including the formulation as described supra, suspended in a solution.

The preparation of the present invention can be suspended in a solution for commercial applications in a spray, drip irrigation, or other water-based delivery system.

Another aspect of the present invention relates to method of treating a plant or a plant seed with a microorganism. This method involves providing a preparation or a formulation as described supra and applying the preparation or the formulation to a plant or plant seed under conditions effective to treat the plant or plant seed.

Treating a plant or a plant seed according to the method of the present invention may include, without limitation, imparting disease resistance, imparting resistance to pests, improving nutrition and/or yield, or any combination thereof.

These aspects of the present invention are further illustrated by the examples below.

EXAMPLES

The following examples are provided to illustrate embodiments of the present invention, but they are by no means intended to limit its scope.

Example 1

Preparation of *Bradyrhizobium* and *Trichoderma* Formulations

Preparation A.

A frozen paste of concentrated *Bradyrhizobium* from a commercial source was used as one starting material and a concentrated conidial spore suspension of *Trichoderma harzianium* strain T22 was used as a second starting material. The initial *Bradyrhizobium* suspension contained about $5\times10^9$ colony forming units/ml of the bacterium. The initial *Trichoderma harzianium* strain T22 suspension contained about $5\times10^8$ cfu/ml. Crystal Tex dextrin was added to the spore suspensions to give a 4% w/v mixture and mixed until it was dissolved. Cellulose (Sigmacell Type 50, Sigma Chemical Co., St. Louis, Mo.) was added to each preparation to give two volumes of cellulose for each volume of cell suspension+Crystal Tex. These were mixed by kneading by hand in a plastic bag until a uniform mixture was obtained. The result was a light green or light tan free-flowing powder for the *Trichoderma* and *Bradyrhizobium* preparations, respectively. The initial water activity (Aw) of the preparations was approximately 0.94. The materials were air dried and the moisture activity levels were 0.44 and 0.55 for the *Trichoderma* and *Bradyrhizobium* preparations, respectively.

Preparation B.

A second preparation was prepared with *Trichoderma harzianum* strain T22. The spore suspensions were centrifuged and gelatinous green pellets were obtained. This was contained in 135 ml, and to provide a workable material, this volume was increased to 250 ml and 3 g of Crystal Tex was dissolved in this. This was mixed with Sigmacell (145 g) and the material was exhausted, so 115 g of another cellulose was used to augment. This material contained larger particles than the Sigmacell material. The result was a green free-flowing, but somewhat clumpy, powder. The material was passed through a 8 mesh sieve to lessen the clumping. The initial water activity of the sample was 1.00, and, after air drying, this decreased to 0.30.

Example 2

Characterization of the Samples

Each of the materials was easily suspended in water. Microscopic examination of the suspension showed a high level of conidia or bacterial cells in the *Trichoderma* or *Bradyrhizobium* preparations, respectively. *Trichoderma* suspensions were placed in potato dextrose broth and incubated with shaking overnight and examined the next morning. All of the conidia swelled and germinated, in contrast with results obtained with spray dried materials.

Plating of either *Trichoderma* preparation A or B gave 3 to $5 \times 10^9$ cfu/g of material, in spite of the fact that preparation B had a higher level of *Trichoderma*, as was evident from both the amount of fungal biomass added and as indicated by the spore color. The cfu/g of the *Bradyrhizobium* preparations were 5 to $8 \times 10^9$ cfu/g.

Part of the reason for this discrepancy was evident by observing preparation B. The material was initially green (which is the color of *Trichoderma* conidia) but after a few minutes, much of the material precipitated as dark green cellulose fibers. Microscopic examination demonstrated that the precipitating cellulose fibers were totally covered with *Trichoderma* conidia (FIG. 1). The plating process measures each particle, whether a single cell or a cellulose fiber coated with thousands of conidia, as a single particle. This is not necessarily a problem for biological activity of the preparation, since it may be that a particle with many spores is equally efficacious, or more so, than a preparation that consists only of single spore cells. The "loaded" particles may provide a more active initial site for activity and growth of the microorganism and since growth is critical for activity, this may be no problem.

The cellulose employed had a large effect upon the binding of spores. Some celluloses are almost totally deficient in this ability while others are very efficient. While not intended to be exclusionary to other materials, it is considered that materials with a high level of hemicelluloses may give higher spore binding than purer celluloses. Either type may be efficacious, depending upon the use envisioned. If free conidia are desirable, then the nonbinding celluloses are preferred. However, it is easy to envision a binding cellulose or hemicellulose+bound spore mixture that then can be coated with a binder or protectant that may be water soluble, insoluble, or that forms a gel. This binding+coating system would provide very high localized concentrations of conidia that could be formulated to be resistant to harsh conditions such as the presence of incompatible chemicals even in water suspensions. Another possibility is to impregnate the cellulose fibers with a *Trichoderma* growth medium that, after further encapsulation, would provide very high levels of *Trichoderma* activity. An example of a use for such a formulation is for use on vegetable seeds, such as those of carrots, onions, or celery. *Trichoderma* requires a nutrient source for germination and growth and these seeds provide very low levels of nutrient exudates, so *Trichoderma* growth is lacking and the seed treatments are ineffective. The nutrient-impregnated *Trichoderma*-binding celluloses provide an excellent delivery system for such materials.

For products to be useful, they must be both biologically active and cost-effective. In the present invention, this has been addressed by testing the efficacy of seed treatments, as described in Example 3.

Example 3

Biological Activity of Preparations

*Trichoderma harzianium* strain T22 formulations were applied to seeds of inbred line Mo17. This particular line responds to effective seed treatments so that there is more rapid growth with the organism than without it. This is an effect that can be measured within 7-14 days after planting seeds in soil (Harman et al., "Interaction Between *Trichoderma harzianum* Strain T22 and Maize Inbred Line Mo17 and Effects of this Interaction on Diseases Caused by *Pythium ultimum* and *Colletotrichum graminicola*," *Phytopathology* 94:147-153 (2004), which is hereby incorporated by reference in its entirety). Further, it is possible to directly observe growth of both T22 and other fungi on seeds within a few days after being placed on moist blotters as seed germination begins.

Of most interest were seed treatments that are highly cost effective, so it was desirable to identify formulations that could be applied to seeds in small amounts while still demonstrating biological activity. Therefore, two rates of application of the preparations were tested (1 oz/cwt and 0.1 oz/cwt). The 1 oz. rate equates to 616 μg of the preparation to 1 g of seeds. For treatment, the formulations described above were suspended in water. The preparations were made at the concentration of 300 mg of formulation in 5 ml of water or, for the lower concentration, a 10× dilution of this concentration. Either of these two concentrations provides a highly economical seed treatment. For corn, at the high rate, 1 pound of formulation would treat sufficient seeds to plant more than 30 acres. This material was applied to seeds either manually with mixing or, for larger seed quantities, in a Hege commercial small batch lab treater. No other stickers or additives were added since the starch used as the encapsulation medium provided excellent adhesion of the material to seeds.

The first tests were evaluations of the growth of T22 on maize seeds (3 days of germination) on blotters, and these results are shown in FIGS. 2A-B. In the photomicrograph labeled "untreated" (FIG. 2A), there is copious growth of contaminating fungi (CF) at the point of attachment of the seed to the cob (at the arrow tip) and by the circular structures on the blotter substrate next to this point. These are fungi that colonized the seed from its production in the field. The sporulation is from *Penicillium* spp., and the circular structures are *Rhizopus* or *Mucor* spp. Contaminating fungi were observed on every nontreated seed but only rarely on seeds treated with T22. Conversely, T22 was observed on every treated seed over much or all of the seed surface, regardless of whether the seeds were treated at the 0.1 or 1 oz. rate, or whether Preparation A or B was used. In FIG. 2B, T22 is seen on the edge of the seed, where contrast for photographic purposes is better than on the seed surface. In this figure, when the picture is larger, typical philades of T22 from the onset of sporulation are evident. This is diagnostic for the presence of T22. Clearly, T22 eliminated the seed-borne contaminating fungi and grew well itself.

The ability of different preparations of T22 was tested with maize inbred line Mo17. The results that follow compared preparation B with a commercial product formulated on a clay base. The cfu levels of preparation B was $2.4\times10^9$ while the cfu level of the commercial preparation was one order of magnitude lower. FIGS. 3A-B demonstrate the efficacy of the two preparations, by comparing heights of maize in mm 10 days after planting, with a total of 30 plants measured. The plants' heights were sorted from smallest to largest with each plant given a number from 1 to 30 depending upon the size of the plants. "Check" refers to plants grown from seeds with no treatment. "RC" refers to plants grown from seeds treated with a cellulose-based formulation, and "RS" is the commercial clay based formulation. RC or RS 1 refers to the 1 oz cwt rate and RC or RS 2 refers to the 0.1 oz rate. The RC formulation gave good growth enhancement at even the 0.1 oz rate, while this rate with the RS formulation was largely ineffective. The 1 oz rate with the RC formulation was probably supraoptimal. Thus, the RC formulations are clearly highly effective—100 lb of seed will plant about two acres, so the amount of the RC formulation to be used per acre is about 0.05 oz.

*Bradyrhizobium* was tested on soybean seeds planted individually in tubular plastic containers with a conical distal end containing holes that allow excess water to flow out of the container to avoid waterlogging of the soil. Measurements included formation of nodules, indicating effective seed treatment. As the plants matured and residual nitrogen was removed from the planting medium, plants with effective nitrogen fixation were evident by a darker green color than plants without nodules and effective nitrogen fixation. The soil used had a low level of native nitrogen-fixing bacteria. Planting in individual plant containers permits identification of rare individual plants from untreated seeds where such native nitrogen-fixing organisms exist. In all cases, seeds were planted in a 1:1 mixture of an Arkport sandy loam field soil: Cornell mix, which is a mixture of peat, vermiculite, perlite and nutrients.

The *Bradyrhizobium* cellulose formulations worked well, with the best results occurring when both T22 and *Bradyrhizobium* were used. Nodulation on 18-day-old soybeans can be measured by the total weight of nodules produced. With T22 and *Bradyrhizobium* together, the nodule weight was 42 mg/plant and when soybean plants were treated with only *Bradyrhizobium*, the nodule weight was only half as great (21 mg/plant).

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. A powder formulation of viable microorganisms comprising:
   (a) microencapsulated microorganisms comprising:
      (i) microorganisms in an amount of at least $5\times10^8$ colony forming units per gram of the formulation, and
      (ii) a water-soluble encapsulating material microencapsulating the microorganisms; and
   (b) a water insoluble, water-absorbent substance that is a dry, free-flowing powder mixed with the microencapsulated microorganisms, the water insoluble, water-absorbent substance present in an amount sufficient to maintain the formulation as a dry, free-flowing powder.

2. The formulation according to claim 1, wherein the water insoluble, water-absorbent substance is selected from the group consisting of zeolite, porous beads or powders, silica, ground agricultural products, porous wood products, cellulose, cyclodextrins, and combinations thereof.

3. The formulation according to claim 2, wherein the water insoluble, water-absorbent substance is cellulose powder.

4. The formulation according to claim 1, wherein the microorganisms are selected from the group consisting of fungi, bacteria, and combinations thereof.

5. The formulation according to claim 4, wherein the microorganisms are fungi.

6. The formulation according to claim 5, wherein one of the fungi comprises a species from the genus *Trichoderma*.

7. The formulation according to claim 4, wherein the microorganisms are bacteria.

8. The formulation according to claim 7, wherein one of the bacteria comprises a species from the genus *Bradyrhizobium*.

9. The formulation according to claim 1, wherein the encapsulating material is present, by total weight of the formulation, in an amount of at least 1% (w/w).

10. The formulation according to claim 1, wherein the encapsulating material is selected from the group consisting of a chitosan, a starch, a glucan, a dextrin, a cellulose which is water soluble, a vegetable or microbial gum, and combinations thereof.

11. The formulation according to claim 1, wherein the water insoluble, water-absorbent substance is present, by total weight of the formulation, in an amount of at least 90% (w/w).

12. A powder formulation of viable bacteria comprising:
   (a) microencapsulated bacteria, comprising:
      (i) bacteria in an amount of at least $5\times10^8$ colony forming units per gram of the formulation, the bacteria comprising at least one species of the genus *Bradyrhizobium*, and
      (ii) a water-soluble encapsulating material microencapsulating the bacteria, the water-soluble encapsulating material selected from the group consisting of a chitosan, a starch, a glucan, a dextrin, a cellulose which is water soluble, a vegetable or microbial gum, and combinations thereof; and
   (b) cellulose powder, mixed with the microencapsulated bacteria, the cellulose powder present, by total weight of the formulation, in an amount of at least 90% (w/w) to maintain the formulation as a dry, free-flowing powder.

13. The formulation of claim 12, wherein the water-soluble encapsulating material is a dextrin.

* * * * *